United States Patent [19]

Goralski

[11] 4,071,547
[45] Jan. 31, 1978

[54] 3-BROMO-2,2-BIS(BROMOMETHYL)PROPYL BROMOMETHANESULFONATE

[75] Inventor: Christian T. Goralski, Midland, Mich.

[73] Assignee: The Dow Chemical Company, Midland, Mich.

[21] Appl. No.: 738,813

[22] Filed: Nov. 4, 1976

[51] Int. Cl.$^2$ .................. C07C 143/68; A61K 31/255
[52] U.S. Cl. ............................... 260/456 R; 424/303
[58] Field of Search ..................................... 260/456 R

[56] References Cited

U.S. PATENT DOCUMENTS 3,978,228  8/1976  Yoshinaga et al. .............. 260/456 R Primary Examiner—Nicky Chan
Attorney, Agent, or Firm—Theodore Post; Daniel L. DeJoseph; C. Kenneth Bjork

[57] ABSTRACT

3-Bromo-2,2-bis(bromomethyl)propyl bromomethanesulfonate. It is useful in the control of the athlete's foot microorganism, *Trichophyton mentagrophytes.*

1 Claim, No Drawings

3-BROMO-2,2-BIS(BROMOMETHYL)PROPYL BROMOMETHANESULFONATE

SUMMARY OF THE INVENTION

3-Bromo-2,2-bis(bromomethyl)propyl bromomethanesulfonate corresponding to the following structural formula

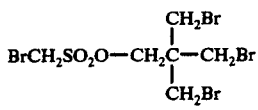

is prepared by reacting at room temperature substantially equimolar proportions of 3-bromo-2,2-bis(bromomethyl)propanol and bromomethanesulfonyl chloride or bromide in the presence of an organic base, advantageously a tri(lower alkyl)amine or pyridine in the presence of a solvent reaction medium, advantageously benzene. The precipitated base hydrochloride or hydrobromide is separated from the reaction medium and the solvent is removed in vacuo to leave a pale orange oil which crystallizes. The crystals are slurried with hexane, filtered off and air dried to give crude ester product which is recrystallized from ethanol to give purified product as fine needles, melting at 86°–88° C.

The ester product, when evaluated for fungicidal activity in the conventional in vitro agar Petri dish dilution test, gave 100% inhibition of Trichophyton mentagrophytes at a concentration of 100 parts per million.

DESCRIPTION OF SOME PREFERRED EMBODIMENTS

The following additional description and example further describe the invention and the manner and process of making and using it to enable the art skilled to make and use the same and sets forth the best mode contemplated by the inventor of carrying out the invention.

EXAMPLE

3-Bromo-2,2-bis(bromomethyl)propyl bromomethanesulfonate

In a one liter three-neck flask equipped with a magnetic stirrer, a nitrogen inlet, a calcium chloride drying tube and an addition funnel were placed 32.5 g (0.1 mol) of 3-bromo-2,2-bis(bromomethyl)propanol, 400 ml of benzene, and 10.1 g (0.1 mol) of triethylamine. The flask was swept with nitrogen. To this solution, a solution of 20.0 g (0.1 mol) of bromomethanesulfonyl chloride in 30 ml of benzene was added dropwise with stirring over a period of 30 minutes. After the addition was complete, the reaction mixture was stirred for 15 minutes and filtered to remove the triethylamine hydrochloride. The triethylamine hydrochloride was washed with several portions of benzene. The benzene was removed in vacuo from the combined filtrates, leaving a pale orange oil which crystallized. The crystals were slurried with hexane and filtered to give, after air drying, 45.4 g of crude ester. The crude ester was recrystallized from ca. 200 ml of absolute ethanol to give 30.8 g of the ester as fine needles, m.p. 86°–88° C.

Anal. Calcd for $C_6H_{10}Br_4O_3S$; C, 14.95; H, 2.09; S, 6.65. Found: C, 14.99; H, 2.06; S, 6.70.

STARTING MATERIALS

3-Bromo-2,2-bis(bromomethyl)propanol is a commercial product which is available from The Dow Chemical Company, Midland, Michigan. Bromomethanesulfonyl chloride is prepared by the method of W. E. Truce et al., J. Org. Chem. 32, 990, 994 (1967). In the preparation, some bromomethanesulfonyl bromide also forms, which reacts in the same way as the corresponding chloride. If desired, bromomethanesulfonyl bromide may be prepared similarly to the method of Truce et al., substituting $PBr_5$ in place of $PCl_5$ in the preparation.

What is claimed is:
1. 3-Bromo-2,2-bis(bromomethyl)propyl bromomethanesulfonate.